(12) United States Patent
Chidambaram

(10) Patent No.: US 8,143,020 B2
(45) Date of Patent: Mar. 27, 2012

(54) ENHANCED METABOLITE GENERATION

(75) Inventor: Devicharan Chidambaram, Middle Island, NY (US)

(73) Assignee: U.S. Department of Energy, Washington, DC (US)

( * ) Notice: Subject to any disclaimer, the term of this patent is extended or adjusted under 35 U.S.C. 154(b) by 461 days.

(21) Appl. No.: 12/417,881

(22) Filed: Apr. 3, 2009

(65) Prior Publication Data
US 2009/0253190 A1 Oct. 8, 2009

Related U.S. Application Data

(60) Provisional application No. 61/042,867, filed on Apr. 7, 2008.

(51) Int. Cl.
| C12P 7/00 | (2006.01) |
| C12P 7/06 | (2006.01) |
| C12P 7/14 | (2006.01) |
| C12P 7/48 | (2006.01) |
| C12P 7/54 | (2006.01) |
| C12P 7/56 | (2006.01) |
| C12P 3/00 | (2006.01) |
| C12P 1/00 | (2006.01) |
| C12P 1/02 | (2006.01) |
| C12P 1/04 | (2006.01) |
| C12P 39/00 | (2006.01) |

(52) U.S. Cl. ........... 435/41; 435/42; 435/69.1; 435/139; 435/140; 435/161; 435/168; 435/170; 435/171

(58) Field of Classification Search ..................... None
See application file for complete search history.

(56) References Cited

U.S. PATENT DOCUMENTS
| 3,226,262 A | 12/1965 | Rohrback et al. |
| 3,331,848 A | 7/1967 | Davis |
| 3,340,094 A | 9/1967 | Helmuth et al. |
| 4,652,501 A | 3/1987 | Bennetto et al. |
| 2009/0017512 A1 * | 1/2009 | May et al. ..................... 435/165 |

OTHER PUBLICATIONS

Holmes et al (Applied and Environmental Microbiology 70:1234-1237, 2004).*
Sakai et al (Biotechnology and Bioengineering 98:340-348, 2007).*
Antoni, D., et al., "Biofuels From Microbes", Appl. Microbiol. Biotechnol. 77:23-35 (2007) (published online Sep. 22, 2007).
Booth, B., "Practical Hydrogen from a Microbial Fuel Cell", ES&T Online News, http://pubs.acs.org /subscribe/journals/esthag-w/ 2005/apr/tech/bb_microbialfuelcell.html (Apr. 27, 2005).
Cazetta, M.L., et al., "Fermentation of Molasses by *Zymomonas mobilis*: Effects of Temperature and Sugar Concentration on Ethanol Production", Bioresource Technology, 98 (2007) pp. 2824-2828 (available online Apr. 8, 2007).
Chaudhuri, S.K., et al., "Electricity Generation by Direct Oxidation of Glucose in Mediatorless Microbial Fuel Cells", Nature Biotech., vol. 21, No. 10, pp. 1229-1232 (Oct. 2003).
"Fermentation of Ethanol", http://www.andrew.cmu.edu/user/jitkangl/Fermentation%20of%20Ethanol/Fermentation%20of%20Ethanol.htm (Jan. 3, 2007).
Gorby, Y.A., et al., "Electrically Conductive Bacterial Nanowires Produced by *Shewanella oneidensis* Strain MR-1 and Other Microorganisms", Proceedings of the National Academy of Science, vol. 103, No. 30, p. 11358-11363 (Jul. 25, 2006).
Gunasekaran, P., et al., "Ethanol Fermentation Technology—*Zymomonas mobilis*", http://www.ias.ac.in/currsci/jul10/articles14.htm., (1999).
Logan, B.E., et al., "Microbial Fuel Cells: Methodology and Technology", Enviro. Sci. & Tech., 2006, vol. 40, No. 17, pp. 5181-5192 (published on Web Jul. 14, 2006).
Lovley, D.R., "Microbial Fuel Cells: Novel Microbial Physiologies and Engineering Approaches", Curr. Op. Biotech., (2006) 17:327-32 (available online May 5, 2006).
Newman, D.K., et al., "A Role for Excreted Quinones in Extracellular Electron Transfer", Nature, vol. 405, pp. 94-97 (May 4, 2000).
Rabaey, K., et al., "Microbial Phenazine Production Enhances Electron Transfer in Biofuel Cells", Enviro. Sci. & Tech., vol. 39, No. 9, pp. 3401-3408 (2005).
Stams, A.J.M., et al., "Exocellular Electron Transfer in Anaerobic Microbial Communities", Enviro. Micro., (2006) 8(3), pp. 371-382).
Tullo, A.H., "Dupont Finds Itself", C&EN, vol. 85, No. 41, pp. 29-30 (Oct. 8, 2007).
Xing, D., et al., "Electricity Generation by *Rhodopseudomonas palustris* DX-1", Environ. Sci. Technol., (published on Web Apr. 25, 2008).

* cited by examiner

*Primary Examiner* — Mary E Mosher
(74) *Attorney, Agent, or Firm* — Joy Alwan; Brian J. Lally; John T. Lucas

(57) ABSTRACT

The present invention relates to the enhanced production of metabolites by a process whereby a carbon source is oxidized with a fermentative microbe in a compartment having a portal. An electron acceptor is added to the compartment to assist the microbe in the removal of excess electrons. The electron acceptor accepts electrons from the microbe after oxidation of the carbon source. Other transfers of electrons can take place to enhance the production of the metabolite, such as acids, biofuels or brewed beverages.

29 Claims, 3 Drawing Sheets

ENHANCED METABOLITE GENERATION

CROSS-REFERENCE TO RELATED APPLICATION

This application claims the benefit of U.S. Provisional Application No. 61/042,867 filed Apr. 7, 2008, which is incorporated herein by reference in its entirety.

This invention was made with Government support under contract number DE-AC02-98CH10886, awarded by the U.S. Department of Energy. The Government has certain rights in the invention.

FIELD OF THE INVENTION

The invention relates to a biological method for improving the rate of removing excess electrons generated by microbial fermentation processes. More specifically, the invention relates to the use of a bacterial culture for the production of metabolic products generated by the utilization of carbon source and also the generation of electricity.

BACKGROUND OF THE INVENTION

Biofuels are produced using microbial fermentation processes. Fermentation is one of the oldest processes known to mankind and can be used to make, interalia, ethanol (or bioethanol). It is cheaper to produce ethanol from petroleum feedstock while albeit more environmentally unfriendly in many regards. However, due to the concern of diminishing availability of fossil fuel, microbial production of biofuel is of significant interest. Traditionally, ethanol has been produced in batch fermentation using yeast strains that cannot tolerate high concentration levels of ethanol. Therefore, strain improvements have been investigated to obtain alcohol-tolerant strains for the fermentation process. The viability of using fermentation for industry-wide production, especially for the production of ethanol, depends on being able to control the fermentation process and overcome some of its inherent shortcomings.

All microbial fermentation processes require a source of energy (a nutrient) to feed the organisms. Typically, the carbon source is used by the microbe for its own energy production. In other words, oxidation of the carbon source provides energy for microbial metabolism.

Fermenting microbes possess varying capabilities of breaking down different carbon-based sources energy. Fermentation processes from any material that contains sugar can be used to produce metabolic products. For example materials for producing ethanol are typically classified under three types of agricultural raw materials: sugar, starch, cellulosic. Sugars, a carbon source, such as sugar cane, sugar beets, molasses or fruits, can be converted to ethanol directly. Starches, e.g., grains, potatoes, or root crops must first be hydrolyzed to fermentable sugars by the action of enzymes from malt or molds. And, cellulosic ethanol is derived from wood, agricultural residues, waste sulfite liquor from pulp and paper mills. These cellulosic materials must also be converted to sugars, in general, by the action of mineral acids or enzymes. After the simple sugar is formed, enzymes from yeast or microbes can readily ferment the sugar (the carbon source) to ethanol. Microbes are currently being engineered to breakdown cellulose directly. Oxidation is by definition the removal of electrons, and thus, those electrons need to be transferred somewhere. These electrons are transferred to an electron acceptor which undergoes reduction, and consequently, maintains the charge neutrality within the microbe. The electron acceptor has to also be regenerated to remove further electrons or be continuously replenished. However, replenishment consumes energy and is not necessary if oxygen is present for example in the ambient atmosphere. Respiratory processes in bacteria are remarkable because of their ability to use a variety of compounds, including insoluble minerals as terminal electron acceptors.

Fermentation processes inherently generate excess electrons within microbes as a result of oxidation of a carbon source by the microbe. The conversion of any carbon source, leads to the generation of excess electrons within the microbes as a result of oxidation of the carbon source. The removal of these excess electrons is a critical molecular mechanism that basically begins within the microbe and typically terminates outside the microbial cell. Examples of some of the molecular mechanisms inherent to microbes include but are not limited to oxygen reduction (transfer to oxygen), organic metabolites reduction, and mineral reduction such as iron or manganese.

Microbes generally have developed evolutionary pathways to dispose of or "remove" excess electrons. Certain microbes even expend energy by secreting electron shuttling compounds to rid the excess electrons that are generated. Further, it has been introduced that microbes produce pili or nanowires for the purpose of removing excess electrons. Various proteins are also believed to be involved in the process of electron transfer by microbes to insoluble materials (e.g., minerals). These proteins include, but are not limited to, outer membrane proteins and periplasmic and extracellular cytochromes. These naturally occurring mechanisms, however, have a kinetically slow rate of removal of the excess electrons.

Many types of bacteria are capable of ethanol formation. However, the microbes will also produce other end products (metabolites) besides ethanol. There is a collection of bacteria that are known to produce primarily ethanol, including but not limited to *Clostridium sporogenes*, *Clostridium indolis*, *Clostridium sphenoides*, *Clostridium sordelli*, *Zymomonas mobilis* ("*Z. Mobilis*"), *Zymomonas mobilis* Sp. *Pomaceas*, *Spirochaeta aurantia*, *Spirochaeta stenostrepta*, *Spirochaeta litoralis*, *Erwinia amylovora*, *Leuconostoc mesenteroides*, *Streptococcus lactis*, *Sarcina ventriculi*. It has been reported that the *Z. mobilis* is a better candidate for industrial alcohol production, and that *Z. mobilis* further possesses advantages over yeast with respect to ethanol productivity and tolerance. *Z. mobilis*, a facultative gram-negative bacterium, is one of the organisms that can be used in large-scale bio-ethanol production.

Bacteria generally grow in nutrient deficient conditions (e.g., soil) and thus, nutrients can be a limiting factor in their metabolism. However, in industrial processes, bacteria are grown in a nutrient rich medium and the naturally occurring molecular mechanism of the bacteria for removing electrons remains a rate limiting factor that may contribute to the inefficiency of the fermentation process to produce ethanol.

One possible solution is to manage glucose limitations by discontinuous feeding of glucose solution. However, a continuous process using co-immobilized amyloglucosidase (AMG) is believed to be a better fermentation process for *Z. mobilis* providing operational stability for over 40 days. Other proposed solutions, include the use of mixed culture of different ethanologenic strains to improve productivity. However, in any case, the continuous or batch methods still rely upon the innate mechanism of the microbe itself and does not address the ability of the microbe to dispose of excess electrons.

Electron acceptors such as anthraquinone disulfonic acid (AQDS) when added as an external (exogenous) electron shuttling agent can also result in a faster kinetics of removing electrons when monitored by the solubilization of an iron oxide. Thus, the mechanism for removing electrons can be altered. There are a number of known electron acceptors, for example, dissimilatory iron reducing microorganisms electron acceptors such as oxygen, metals, extracellular quinines, quinones (e.g., AQDS), sulfur compounds, nitrate, fumarate, chlorinated compounds, and electrodes can be used. However, it is reported that the addition of organic redox mediators does not always enhance the reduction of insoluble iron to the same extent. Thus, it is not certain how or albeit even if an electron acceptor will have an effect on reduction of metal or as an electron acceptor in general for a given microbe in the reduction of metal. It is also reported that electric potential or current applied to cells, tissues and organisms results in the ability to stimulate their metabolic pathways (e.g., cell growth and glucose breakdown or utilization). This has been demonstrated for a high active strain of *Streptomyces noursei* ZIMET 43716, and yeast. Further, there are mutants of *Shewanelia putrefaciens* that are unable to respire on humic substances.

Research has also been carried out for optimizing fermentative organisms, low-cost substrates, and environmental conditions for fermentation to occur. As an illustration, a strain improvement program recognized the need to obtain an alcohol-tolerant strain for the fermentation process. The cells are recycled in fermentation by immobilization in a suitable matrix.

It has also been reported that microbial fuel cells (MFCs) can harvest electricity from an organic matter stored in marine sediments. Additional studies related to these systems, has introduced the concept that microorganisms conserve energy to support their growth by completely oxidizing organic compounds to carbon dioxide with direct, electron transfer to electrodes suggesting that self-sustaining MFCs are feasible. It is also reported that many applications of MFCs rely on the selection of electricity-producing microorganisms from the natural community of microbes in the organic source material. However, the exploration of these systems has failed to recognize an effect, if any, that these same electricity-producing microorganisms have in metabolic product generation based on glucose utilization.

Typically, the microbes for producing electricity in MFCs are different types of microbes than the fermenting microbes for generating metabolic products based on glucose utilization. The electricity producing microbes degrade glucose to carbon dioxide while the microbes used for metabolic product generation degrade glucose to the level of a simpler substance such as ethanol.

One of the main bottlenecks experienced with MFCs is the electron transfer from the bacteria to the anode. A transfer resistance is caused by either oxidizing a compound at the anode surface or reducing a compound at the bacterial surface or in the bacterial interior surface that can require a certain energy to active the oxidation reaction. Transfer resistance results in potential losses between the bacteria and the electrodes, generally referred to as over potentials. Thus, the build up of excess electrons is a phenomenon recognized in the field of MFCs.

There remains a need to further expand and enhance the mechanism for metabolic product generation derived from glucose utilization as well as for current generation. To this end, the present invention relates to a method of removing electrons by providing a conduit for the transfer of electrons produced during the fermentation process and thereby enhancing the rate of production of metabolites derived from glucose utilization in addition to the generation of useful electricity.

SUMMARY OF THE INVENTION

The invention relates to methods associated with the ability to enhance the rate of a microbial-based fermentation process that produces metabolic products. The steps of the methods include initially oxidizing a carbon source with at least one microbe. The at least one microbe is capable of fermentation in at least one compartment having at least one portal. An electron acceptor is added to accept electrons from the fermenting microbes after oxidation of the carbon source. As a further step, the accepted electrons are transferred from an electron shuttling compound or redox active species to at least one solid electrode.

Additional methods include enhancing the production rate of metabolic products generated by glucose utilization using the electron shuttling compound, the solid electrode or the redox active species as the electron acceptor. And, another method includes the generation of current using the above-mentioned steps.

In a method of the invention current is generated as a result of a system that enhances the production rate of at least one metabolite. A carbon source is oxidized with at least one microbe capable of fermentation in at least one compartment with at least one portal, at least one electrode is added to accept electrons from the at least one microbe after oxidation of the carbon source, wherein the at least one electrode comprises at least one anode connected to at least one cathode.

The invention also relates to a method of enhancing the production rate of an alcohol by oxidizing a carbon source with *Zymonomas mobilis* in at least one compartment with at least one portal. At least one electron acceptor is added to accept electrons from the at least one microbe after oxidation of the carbon source. The electrons are transferred to at least one electrode having an anodic region.

The invention includes a system having compartments as described above comprising the microbe capable of fermentation, the carbon source and the electron acceptor in the compartment wherein the electron acceptor accepts electrons from the microbe capable of fermentation after the carbon source is oxidized.

DETAILED DESCRIPTION OF THE INVENTION

Figure 1:
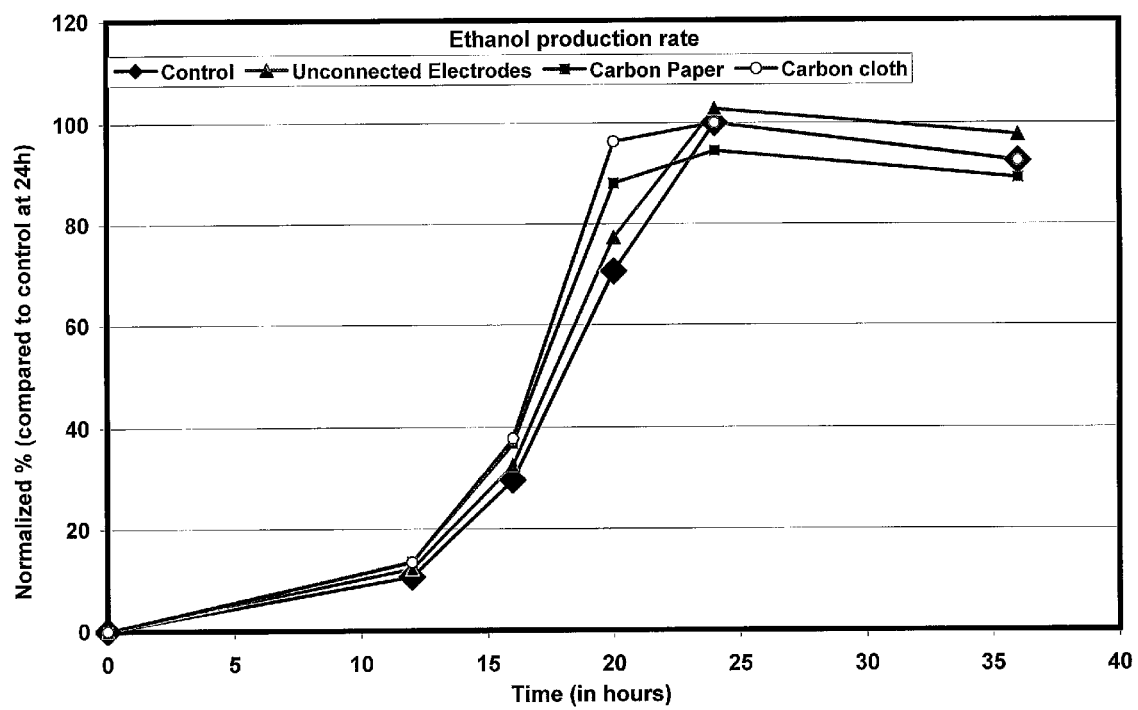
FIG. 1 is an unnormalized chart comparing the rate of ethanol production over a period of more than 35 hours for a control, a system using two unconnected carbon paper electrodes, a system using two connected carbon paper electrodes, and a system using two connected carbon cloths.
Figure 2:
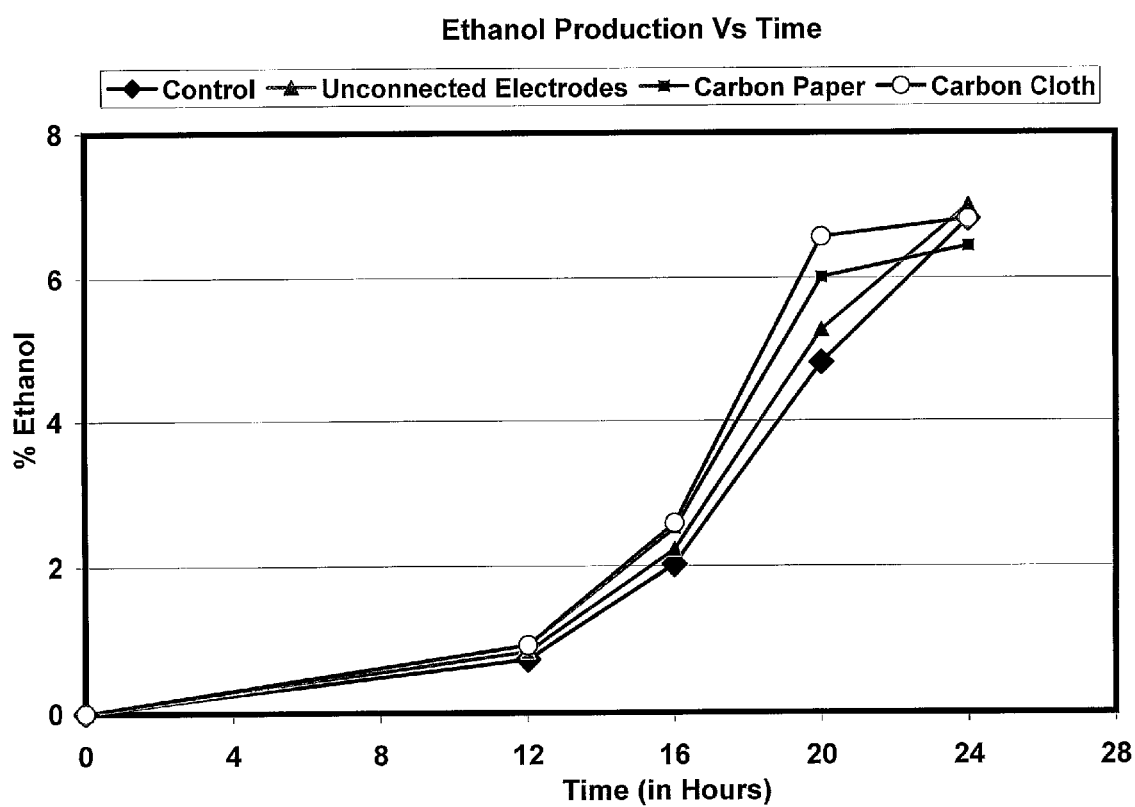
FIG. 2 is an unnormalized chart comparing the rate of ethanol production for a period of 24 hours for a control, a system using two unconnected carbon paper electrodes, a system using two connected carbon paper electrodes, and a system using two connected carbon cloths.
Figure 3:
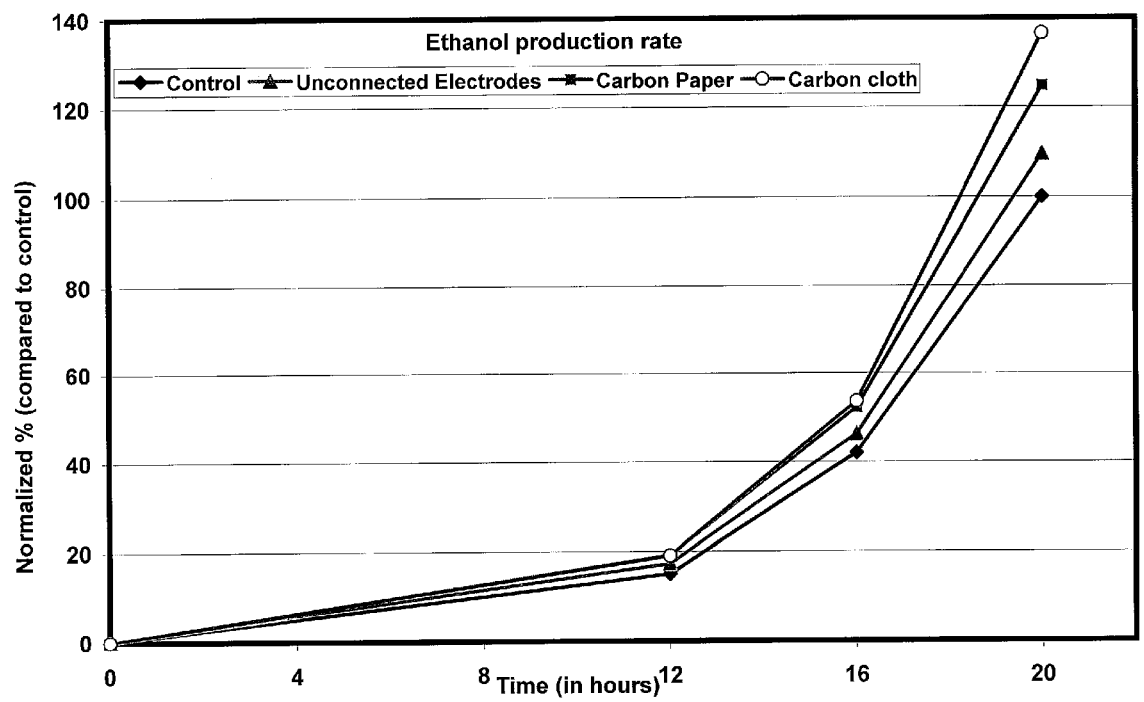
FIG. 3 is a normalized chart comparing the rate of ethanol production for a period of 20 hours for a control, a system using two unconnected carbon paper electrodes, a system using two connected carbon paper electrodes, and a system using two connected carbon cloths.

This invention relates to enhancing the rate of electron removal by the microbe in a system that uses a microbially-based fermentation process to produce at least one metabolite. As used herein fermentation means any process in which a microbe causes or contributes to a breakdown of a complex organic substance into simpler substances. The system can produce metabolic products including but not limited to hydrogen, citric acid, acetic acid, alcohol as a biofuel, particularly ethanol or butanol, or as a brewed beverage, particularly ethanol. For example, *Clostridia* sp. typically produces hydrogen in addition to ethanol. The metabolic product is not carbon dioxide. In addition, the system can be one where current is generated. The acceleration of the electron removal processes of the fermenting microbe thereby renders a rate increase in the production of metabolites. There are several steps towards this enhanced rate of removing electrons.

The first step of the present invention is oxidizing a carbon source with at least one microbe capable of fermentation in at least one compartment. In general, the microbe in the system is any fungus, yeast or bacteria (e.g., aerobic or anaerobic gram negative or positive microorganism) that is capable of fermentation. As used in the present specification, the term microbe includes any microorganism per se as well as any microorganism that is genetically manipulated (modified) or mutated (mutagenesis) to improve its performance as a microbe for the production of smaller substances after the breakdown of a complex organic substance (e.g., glucose) by the process of fermentation and any cloned genes of the microorganism that may be conjugated either by transforming the microorganism with genes of interest acquired from other organisms or by transferring genes from the microorganism (e.g., those involved in syntheses of the smaller substance) to other organisms. The smaller substances can be for example, hydrogen, acetic acid, citric acid, lactic acid, alcohol (e.g., industrial alcohol, drinking alcohol, biofuel) or other biofuels.

The microbe is capable of fermentation to produce alcohol. Preferably, the alcohol is ethanol generated by the breakdown of glucose by the microbe and can be either a biofuel or a brewed beverage. Thus, the metabolite is a biofuel or a brewed beverage, and particularly, in the form of ethanol or butanol as an alternative biofuel. More preferably, the microbe is one that is ethanologenic (i.e., uses glucose, fructose, and sucrose or other sugar sources as its nutrient and generates ethanol as a primary metabolic product of the fermentation process) or butanologenic. For the generation of ethanol, the microbe is one that has a plasma membrane that contains hopanoids, and pentacyclic compounds similar to eukaryotic sterols. This allows the microbe to have an extraordinary tolerance to ethanol in its environment, about 13%.

The microbe is for the generation of ethanol, a facultative gram negative bacteria and preferably is of the *Zymomonas* sp. The *Zymomonas* sp. is preferably *Zymomonas Mobilis* (ATCC no. 31821; hereinafter *Z. Mobilis*) obtained from ATCC 29191, ATCC 10988, ATCC 12526, or NRRL B4286. *Z. Mobilis* is a facultative gram negative bacteria that is osmo- and ethanol-tolerant and has been shown to have higher specific rates of glucose uptake and ethanol production via the Entner-Doudoroff pathway under anaerobic conditions than other microbes. The genome size of *Z. mobilis* strains is in the range of $1.53+0.19 \times 10^9$ Da, about 56% of the *E. coli* genome, and can accommodate about 1500 cistrons. The DNA base composition of *Z. mobilis* (48.5+1.0% G+C) was determined by thermal denaturation. The microbe can be combined with a second microbe.

The carbon source for *Z. mobilis* can be Glucose: 20 g; Yeast Extract 10 g; and $KH_2PO_4$ 2 g. In the fermentation process, where the microbe uses the carbon source as a nutrient, alcohol, such as ethanol or butanol, is produced. In addition to producing alcohol, excess electrons are generated that the microbe must remove. The microbe has inherent processes for the removal of the excess electrons. But, these mechanisms are slow and render the microbe less able or indeed in some cases unable to produce alcohol by the fermentation process for the period of time in which it is removing excess electrons.

The step of oxidizing takes place in at least one compartment. The at least one compartment has at least one portal that can act as an inlet, outlet, or both an inlet and an outlet. The inlet permits the inward flow of the carbon source (or media contents) for the microbes whereas the outlet permits the outward flow of the metabolic product (metabolite) for removal. The compartment can be part of a microbial fuel cell system.

The at least one compartment does not contain a physical barrier to the microbe. More than one compartments or chambers are created by having the electron acceptor comprise an electrode having at least one anode connected to at least one cathode, and by dividing the at least one compartment with at least one physical barrier to the microbe. The physical barrier acts as a barrier to the microbe but not to the media in the compartments. The compartments are so divided into at least one anode chamber containing the anode and the at least one microbe, and at least one cathode chamber containing the cathode and that is substantially bacteria-free. As the anode is connected to the cathode, in addition, current can be generated.

The second step of the present invention is adding at least one electron acceptor to accept electrons from the microbes after oxidation of the carbon source. The benefit of this step is that the removal of excess electrons produced by the microbe is enhanced. Without this step, the ability of the microbe to produce the metabolic product by the fermentation process diminishes. However, with the present invention, metabolite generation is enhanced by assisting the microbe in its removal of excess electrons. The electron acceptor can be the terminal acceptor of electrons or it can be the intermediary acceptor of electrons (i.e., the electrons are further transferred to an electrode). Specifically, the electron acceptor can be an electrode, a 3-D conducting electrode material, an electron shuttling compound, or a redox active species.

The present methods include enhancing the production rate of a metabolite with the steps of oxidizing the carbon source and adding at least one electron shuttling compound to accept electrons from the microbe after oxidation of the carbon source. The electron shuttling compound is preferably a benign soluble redox electron transfer shuttle agent. More preferably, the electron shuttling compound is quinines, or quinines (e.g., AQDS). The electron shuttling compound can also accept electrons from the electrode or the 3-D conducting material; and can also transfer electrons to the electrode. Thus, the electron shuttling compound can, if the electron acceptor also includes an electrode, transfer the electrons to the electrode. Electrons can be transferred to the anodic region of the electrode or to the anode. The electron shuttling compound is exogenously added to the compartment or if it is secreted by the microbe it is in combination with one of the other added electron acceptors.

The present methods include enhancing the production rate of a metabolite comprising the steps of oxidizing the carbon source and adding at least one redox active species to accept electrons from the microbe after oxidation of the carbon source. The redox active species can be for example, $Fe^{+3}$ that can accept electrons.

The 3-D conducting electrode material can, if the electron acceptor also includes an electrode, transfer the electrons to the electrode. Electrons can be transferred to the anodic region of the electrode or to the anode.

The present methods include enhancing the production rate of a metabolite comprising the steps of oxidizing the carbon source and adding at least one solid electrode to accept electrons from the microbe after oxidation of the carbon source. The at least one electrode (i.e., solid electrode) has either an anodic region and a cathodic region or at least one anode connected to at least one cathode. When the anode is connected to the cathode the method of enhancing the production rate of the metabolite further comprises the step of generating current.

The electrode is composed of a conductive material such as for example, carbon paper, carbon cloth (fabric), carbon fiber (standard, chopped or milled), carbon foam, carbon pellet, carbon mat, or carbon braid. The conductive material is preferably composed of conductive carbon (i.e., is electrically conductive) to act as an electron acceptor for the microbe or to transfer electrons from the microbe to a solid electrode. The transport of electrons is facilitated by the carbon that is conductive. Bacteria can approach and interact or stick to carbon because carbon is microbially friendly.

Specifically, the cathode can be Pt (platinum) foil or Pt mesh, or Ir (iridium) alloy mesh. Also, the cathode can be Pt containing carbon paper.

The conductive material is known to be used alternatively as a gas diffusion material in fuel cells. The gas diffusion materials have an open pore structure, and exhibit high electrical conductivity. Gas diffusion materials are made electrically conductive by embedding highly conductive materials in a mesh matrix made of for example, woven cloth, non-woven paper or felt.

The conductive material of the present invention can be treated or untreated. Preferably, the electron acceptor is carbon cloth or carbon paper. As used herein the term carbon paper refers to a system where one or two carbon electrodes are connected through a load (i.e., resistance with a copper wire) and each electrode is carbon paper. Similarly, as used herein, the term carbon cloth refers to a system where one or two electrodes are connected through a load (i.e., resistance with a copper wire) and each electrode is carbon cloth. Preferably, the electrode is an untreated conductive material.

Preferably, the conductive carbon of the conducting material has a high surface area. The term "high surface area" as used herein refers to a surface area of the conductive carbon in the conductive material such as the carbon cloth or carbon paper that is accessible by the microbe and that is greater than the surface area of the conductive material per se.

The surface area of the conductive material per se refers to the dimensions of the conductive material used to calculate its surface area, whereas the surface area of the conductive carbon refers to the access that the microbes have to the conductive carbon on the conductive material which can be equal to or greater than the surface area of the conductive material. As an illustration, if the conductive material is a triangle and is porous, the conductive material per se may have a surface area measured by one-half times the base times the height of the triangle (the calculated area of the triangle). However, the surface area of the conductive carbon may be greater than the area of the triangle (the conductive material) because the surface area of the conductive carbon is not just on the surface of the conductive material but also within the pores of the conductive material.

Increasing the surface area of the conductive material renders an increase in the rate of reaction between the microbe and the conductive material to transfer electrons. Therefore, the rate of electron acceptance is enhanced with a larger surface area. The larger surface area provides more of an area to transfer electrons and enhances the electron removal process for the microbe. The surface area can be as small as it is possible to construct or in the case of carbon paper to cut; and can be as large as the dimensions of the compartment holding the electrode.

When there is one compartment and if oxygen is present to accept the electrons, a single electrode with the anodic and cathodic regions can be used. The batch reactor (i.e., the single compartment with a single portal opening) is typically anoxic on the bottom of the compartment where the microbes generate the biofuel and the top of the surface is exposed to the atmosphere (oxygen). By placing the anode at the bottom of the reactor, electrons can be accepted as an intermediate and then transferred through the electrode to the top of the surface where the electrons are given to the oxygen, the electron acceptor. This can be achieved using an electrode where the anodic region of the electrode is lower than the cathodic region of the electrode. Preferably, the electrode is shaped in a single curve. More preferably, the electrode is c-shaped.

In one compartment, alternatively, two electrodes can be used. In this case, the at least one electrode comprises at least one anode (i.e., acceptor electrode) and at least one cathode (i.e., donor electrode). The anode is connected to the cathode. The anode and the cathode are preferably arranged in a manner such that the bacteria is separated from the cathode and is accessible to the anode. For example, in a single compartment the cathode is placed horizontally near the top surface of the compartment to enhance its access to oxygen in the atmosphere and the media, and the anode is placed near the deep bottom of the compartment to enhance its access to the microbes. The two electrodes are connected via a resistance or load where electricity (i.e., current flows) is generated.

When the compartment is arranged as a two compartment system having two electrodes, one electrode is in an anode chamber and the other electrode is in a cathode chamber, with at least one physical barrier that acts as a semi-permeable membrane through which, for example, protons or neutral molecules can pass separating the anode chamber and the cathode chamber but through which bacteria (i.e., the microbe) cannot pass. Another type of physical barrier that can be used with this system is a proton exchange membrane (also referred to as a polymer electrolyte membrane or PEM). The PEM is a semipermeable membrane that is generally made of ionomers and is designed to conduct protons but is impermeable to gases such as oxygen or hydrogen. The anode accepts electrons from the bacteria in the anode chamber and the electrons travel through a resistance generating useful current. The cathode receives the electrons in the cathode chamber which is substantially bacteria free.

Electron shuttling compounds or redox active species such as AQDS or $Fe^{+3}$ can be added to the anode chamber. To maintain charge neutrality the compartments can be connected indirectly using a salt bridge or be connected directly. When connected directly, a semi-permeable membrane is used to keep the bacteria in the anode chamber (which is anoxic) away from the cathode chamber (which is exposed to oxygen). Preferably, when the microbe is anaerobic it is present in a two compartment system. In another embodiment of the present invention, the compartment is arranged in a continuous parallel/counter flow treatment design. The compartment can be divided into two sectional chambers with the semi-permeable membrane in-between the anode chamber and the cathode chamber.

EXAMPLES

*Zymomonas Mobilis* (ATCC no. 31821) is obtained from ATCC. This culture is maintained in sterilized media prepared as follows. To 1 liter of deionized 18.2 MΩ 'millipore' water add Glucose: 20 g; Yeast Extract 10 g; and $KH_2PO_4$ 2 g. Stir contents well over magnetic stirrer for 10 minutes and adjust pH to 6.05 using about 2 ml NaOH. Then dispense 50 ml each of the sterilized media into twenty (20) 125 ml Erlenmeyer flasks. Cap the mouth of the 20 Erlenmeyer flasks with cotton plugs. Cover each of the 20 Erlenmeyer flasks with aluminum foil and autoclave them at 121° C. for 15 minutes.

To maintain the culture, 3-4 ml of inoculum from a stationary phase culture is added to these flasks and maintained in an incubator at 26° C. This is the 'maintenance culture'.

Fermentation experiments are conducted in a rich glucose media which is prepared as follows. To 1.1 liter of deionized 18.2 MΩ 'millipore' water add Glucose 110 g; Yeast Extract 11 g; $KH_2PO_4$ 1.1 g; $(NH_4)_2SO_4$ 1.1 g; and $MgSO_4.7H_2O$ 0.55 g. Stir contents well over magnetic stirrer for 10 minutes and adjust pH to 6.05 using about 2 ml NaOH. Then dispense 132 ml into each of four (4) 250 ml Erlenmeyer flasks (labeled 'bac') and 143 ml into each of four 250 ml Erlenmeyer flasks (labeled 'no-bac'). Cap the mouth of each of the Erlenmeyer flasks with cotton plugs. Cover the flasks with aluminum foil and autoclave them at 121° C. for 15 minutes.

The two compartment systems used in the experiment are assembled with a 0.2 □m micron polycarbonate membrane (GE), plugged with cotton, covered with aluminum foil and autoclaved at 121° C. for 15 minutes. A stirrer bar is present in each compartment. To perform actual experiments, the 'maintenance culture' is grown fresh for 24-28 hours prior to the experiment. Then 11 ml of this culture is transferred to the 'bac' flasks and shaken under sterile conditions. First, 71.5 ml from the 'bac' flask is then dispensed to one compartment (anode chamber) in each of the control and an experimental 'two-compartment' system. Then 71.5 ml of "no bac" is dispensed into the empty compartment (cathode chamber) in each of the control and the experimental 'two compartment' system. All transfers are done under sterile conditions.

In the case where electrodes are used, the carbon paper/carbon cloth act as the electrodes. Etek, Inc., BASF Fuel Cell, Somerset, N.J. of approximately 2 cm×7.5 cm dimensions with a connector formed by a conductive carbon tape are autoclaved at 121° C. for 15 minutes and transferred to the experimental cells in an aseptic manner. When necessary the connectors from these electrodes are connected. The potential and current are monitored and recorded using standard ammeters and voltmeters.

Samples from each compartment are taken periodically (after stirring them for 1 minute by means of a magnetic stirrer) in an aseptic manner and diluted 20 times and analyzed for ethanol and glucose concentrations using HPLC and cell growth (600 nm optical density) using UV-Visible spectrometer. These are standard well-established protocols.

Although the invention has been described relative to exemplary preferred embodiments thereof, it will be understood by those skilled in the art that variations and modifications of these embodiments can be effected without departing from the scope and spirit of the invention.

The invention claimed is:

1. A method of enhancing the production rate of at least one metabolite comprising the steps of
   a) oxidizing a carbon source with at least one microbe capable of fermentation in at least one compartment with at least one portal,
   b) adding at least one electron acceptor to accept electrons from the at least one microbe after oxidation of the carbon source, and
   c) transferring electrons from the electron acceptor to an electrode with an anodic region and a cathodic region wherein transfer of the electrons enhances the production of metabolites.

2. The method of claim 1 wherein the metabolite is selected from the group consisting of hydrogen, citric acid, acetic acid, lactic acid, alcohol, other biofuels, and combinations thereof.

3. The method of claim 1 further comprising the step of generating current.

4. The method of claim 1 wherein the at least one electron acceptor is an electron shuttling compound continuously transporting electrons between the microbe and the anode.

5. The method of claim 4 wherein the electron shuttling compound is selected from the group consisting of, quinones, and quinines and combinations thereof.

6. The method of claim 4 wherein the electron shuttling compound is a microbially friendly soluble electron transfer shuttle agent.

7. The method of claim 1 wherein the at least one compartment does not contain a physical barrier to the microbe.

8. The method of claim 1 where the electrode further comprises the anodic region lower than the cathodic region.

9. The method of claim 8 where the electrode further comprises a single curved shape.

10. The method of claim 1 wherein the at least one compartment further comprises the electron acceptor comprising at least one anode directly connected to at least one cathode, at least one physical barrier to the microbe dividing the at least one compartment into at least one anode chamber containing the anode and the at least one microbe and at least one cathode chamber containing the cathode and that is substantially bacteria-free.

11. The method of claim 10 further comprising the step of generating current.

12. The method of claim 10 wherein the electron acceptor further comprises an electron shuttling compound.

13. The method of claim 10 wherein the electron acceptor further comprises a redox active species.

14. The method of claim 10 wherein the electron acceptor further comprises a 3-D conducting electrode material.

15. The method of claim 1 wherein the electrode is a solid electrode having an anodic region and a cathodic region.

16. The method of claim 15 wherein the electrode is an untreated conductive material.

17. The method of claim 15 wherein the electrode is a conductive material in the form of carbon paper, carbon cloth, carbon fiber, carbon foam, carbon pellet, carbon mat, or carbon braid.

18. The method of claim 15 wherein the electrode is a conductive material having a high surface area.

19. The method of claim 1 wherein the microbe is a fungus, yeast, a gram negative bacteria or a gram positive bacteria.

20. The method of claim 1 wherein the microbe is a facultative gram negative bacteria.

21. The method of claim 1 wherein the microbe is from the *Zymomonas* sp.

22. The method of claim 1 wherein the microbe is *Zymomonas mobilis*.

23. The method of claim 1 wherein the microbe is from the *Zymomonas* sp. and is combined with a second microbe.

24. The method of claim 1 wherein the microbe is genetically modified or mutated.

25. The method of claim 1 wherein the at least one compartment is part of a microbial fuel cell system.

26. A method of enhancing the production rate of at least one metabolite comprising the steps of
   a) oxidizing a carbon source with at least one microbe capable of fermentation in at least one compartment with at least one portal,
   b) adding at least one redox active species to accept electrons from the at least one microbe after oxidation, and
   c) having an electrode containing an anode region and a cathode region to receive electrons from the redox active species.

27. The method of claim 26 wherein the metabolite is selected from the group consisting of hydrogen, citric acid, acetic acid, lactic acid, alcohol, other biofuels, and combinations thereof.

28. The method of claim 26 wherein the redox active species is $Fe^{+3}$.

29. The method of claim 4 wherein the electron shuttling compound is anthraquinone disulfonic acid (AQDS).

* * * * *